United States Patent [19]

Kleinerman

[11] Patent Number: 5,706,808
[45] Date of Patent: Jan. 13, 1998

[54] FIBER OPTIC SYSTEM FOR MEASURING CARDIAC OUTPUT

[76] Inventor: Marcos Y. Kleinerman, 24 Jerome St., Southbridge, Mass. 01550

[21] Appl. No.: 381,132

[22] Filed: Jan. 31, 1995

[51] Int. Cl.⁶ .................................................. A61B 5/00
[52] U.S. Cl. .................. 128/634; 128/692; 128/713
[58] Field of Search ...................... 128/633–635, 128/692, 664–666, 667, 713; 607/92; 604/52

[56] References Cited

U.S. PATENT DOCUMENTS

| | | | |
|---|---|---|---|
| 4,476,870 | 10/1984 | Peterson et al. | 128/665 |
| 4,703,757 | 11/1987 | Cohen | 128/667 |
| 4,735,212 | 4/1988 | Cohen | 128/667 |
| 4,873,989 | 10/1989 | Einzig | 128/692 |
| 5,048,524 | 9/1991 | Bailey | 128/634 |
| 5,379,764 | 1/1995 | Barnes et al. | 128/664 |
| 5,458,128 | 10/1995 | Polanji et al. | 128/665 |
| 5,460,182 | 10/1995 | Goodman et al. | 128/665 |
| 5,494,031 | 2/1996 | Hoeft | 128/665 |

FOREIGN PATENT DOCUMENTS

| | | | |
|---|---|---|---|
| 0012537 | 11/1990 | WIPO | 128/692 |

*Primary Examiner*—Angela D. Sykes

[57] ABSTRACT

The method subject of the invention is based on fiber optic technology, and in particular on the light transmission changes at a wavelength or wavelengths $\lambda_s$ within an optical absorption band of hemoglobin occurring over a length of bare core of an optical fiber, inserted in an artery and covered with the patient's blood, when a clear aqueous saline or dextrose solution, optically transparent at said wavelength or wavelengths $\lambda_s$, displaces much of the blood as it flows around the fiber core under the heart's pumping action.

6 Claims, 1 Drawing Sheet

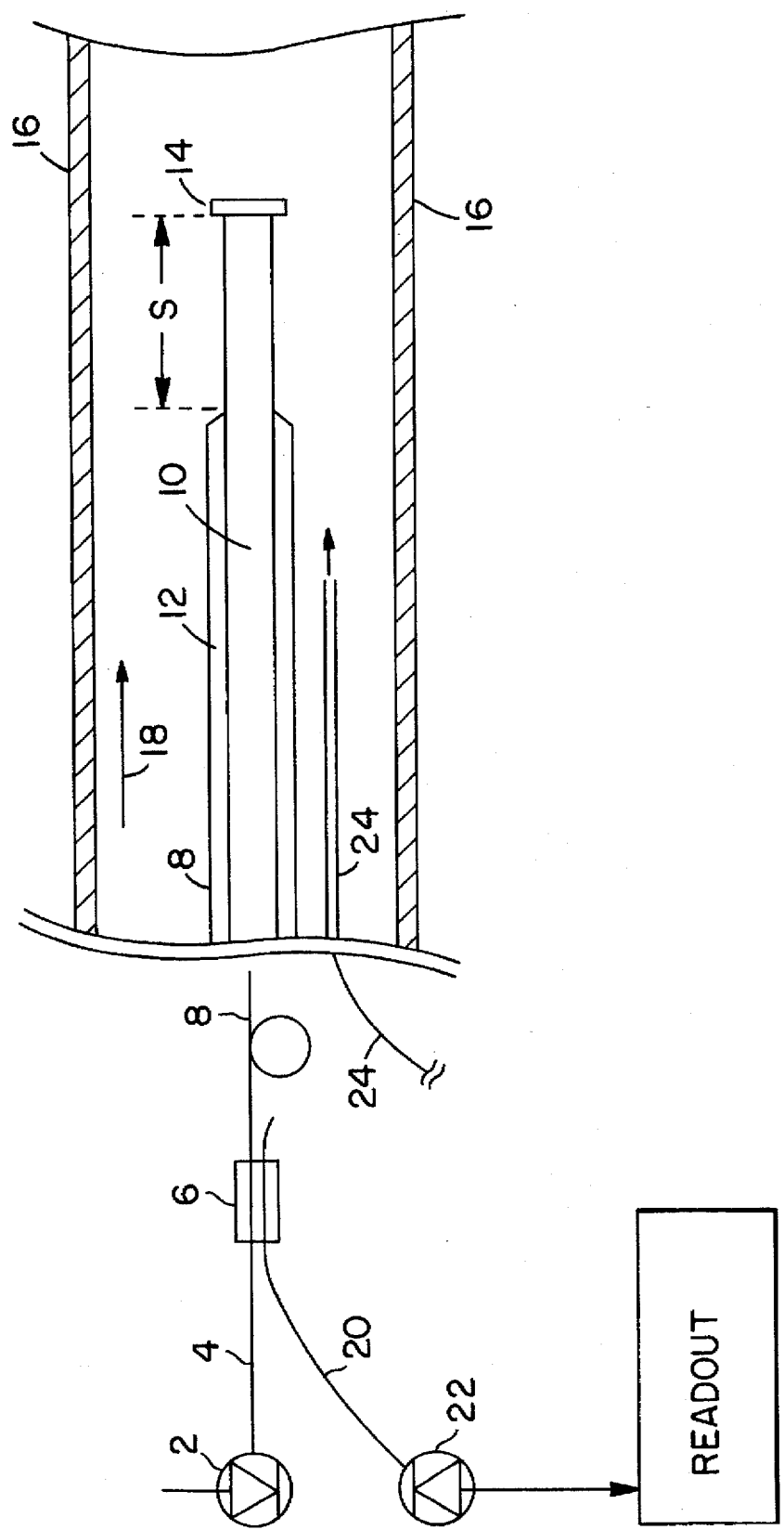

FIBER OPTIC SYSTEM FOR MEASURING CARDIAC OUTPUT

BACKGROUND OF THE INVENTION

The present invention relates to improved methods and devices for measuring cardiac output using fiber optic techniques.

DESCRIPTION OF THE PRIOR ART

Cardiac output is measured conventionally by the thermodilution technique. A bolus of cold fluid, typically 10 milliliters of a saline solution or a 5% aqueous solution of dextrose, is injected into the circulating blood before the right or the left side of the heart, a fixed distance away from a temperature probe towards which the blood and the cold fluid flow. As the cold fluid flows towards the probe (in the pulmonary artery or the aorta), it is gradually diluted by the warmer blood. The cardiac output is determined from the time dependence of the temperature measured by the temperature probe and from the changes in the intravascular heat content. An extensive treatment of the thermodilution method is given in chapter 14 of the book "DYE CURVES: THE THEORY AND PRACTICE OF INDICATOR DILUTION" edited by Dennis A. Bloomfield, University Park Press (1974). The cardiac output by thermodilution can be calculated from the following formula:

$$CO = V_1 \times (T_b - T_1) \times S_1 \times C_1 \times 60 / [S_b \times C_b \times \int T_b(t)dt] \quad 1)$$

where

CO is the cardiac output in ml/minute, $V_1$ is the volume of injectate in ml, $T_b$ is the blood temperature in °C., $T_1$ is the mean temperature in °C. of the injectate at the point of entrance into the blood stream, $S_1, S_b$ are the specific gravity of injectate and blood, respectively, in g/cm$^3$, $C_1, C_b$ are the specific heat of injectate and blood, respectively, in cal/g/°C., and $\int T_b(t)dt$ is the area of the thermodilution curve in seconds x °C.

It follows from equation (1) that there is a plurality of thermal variables which can affect the measurement. In order to minimize errors it is necessary, among other things, to rigorously control and keep constant the temperature of the injectate. There are other sources of error. If the temperature probe (usually a thermistor) is wedged against the arterial wall the thermodilution curve will be distorted. Then there are differences in blood temperature in different sections of the circulation. Additionally, the temperature changes associated with the thermodilution method are relatively small, requiring relatively high accuracy in the temperature measurements.

An alternate method, used in the past before being essentially superseded by the thermal dilution method, is the dye dilution method, whereby a solution of a highly light-absorbing organic dye, typically Indocyanine Green (ICG), also known as "Cardio Green", is injected instead of the cold fluid. One of the drawbacks of the dye dilution method, which contributed to its falling out of favor, is spectral fading caused by blood chemicals which may appear under some pathological conditions. Another is the distortion of the dye dilution curve by recirculation, an effect which is absent in the thermodilution method.

OBJECT OF THE INVENTION

It is an object of the invention to provide a simple method and a device for the optical measurement of cardiac output which is essentially independent of temperature and does not use any injected dye solution. Since it is essentially independent of temperature, it is not affected by the thermal sources of error mentioned above.

SUMMARY OF THE INVENTION

The method subject of the invention is based on fiber optic technology, and in particular on the light transmission changes at a wavelength or wavelengths $\lambda_s$ within an optical absorption band of hemoglobin occurring over a length of bare core of an otherwise ordinary optical fiber, inserted in an artery and covered with the patient's blood, when a clear aqueous saline or dextrose solution, optically transparent at said wavelength or wavelengths $\lambda_s$, displaces much of the blood as it flows around the fiber core under the heart's pumping action. The core of the fiber, though bare, is intact, neither broken nor otherwise modified from its elongated cylindrical shape. The preferred wavelengths $\lambda_s$ at which the light is most strongly absorbed by the hemoglobin of the blood red cells are within the spectral band peaking at near 505 nanometers (nm). Other preferred wavelengths $\lambda_s$ are within a weaker absorption band peaking at near 800 nm.

As known in the art, when a fiber with a bare core having an index of refraction $n_1$ is immersed in any medium, that medium acts as an effective cladding on said "bare" core, with an index of refraction $n_2$. The numerical aperture NA of the fiber, a measure of the number of optical modes the fiber can carry, is given by the relation $$(NA) = (n_1^2 - n_2^2)^{1/2}$$

In order for an optical fiber to confine the light within the core the value of (NA) must be positive. Light travels along a fiber core because of the phenomenon of "total internal reflection" at the core/cladding boundary. Actually the picture is less simple, in that each light reflection involves a penetration into a layer of the cladding of a thickness of the order of a light wavelength. This is called the "evanescent" layer. Therefore, a cladding must be optically homogeneous and transparent at the wavelengths of the light being conducted by the fiber. The value of $n_1$ in most commercial fibers is greater than 1.458, the index of refraction of pure silica at the wavelength of the Na yellow light, 589 nm. This is substantially higher than the index of refraction of blood serum, in which the hemoglobin-containing red blood cells are suspended.

Now, as blood (or any other liquid having an index of refraction lower than that of the fiber core) flows over a bare fiber core, the light being conducted by the core penetrates into the evanescent layer of the liquid. If there are any light-absorbing or light-scattering molecules or particles in the evanescent layer, a fraction of the intensity of the light being conducted by the fiber core is lost by absorption or scattering at the evanescent layer. Because the light wavelength in the system of this invention is chosen within an absorption band of the hemoglobin of the red blood cells, the light loss will be greater (and the intensity of the transmitted light lower) when the bare fiber core is covered by flowing blood than by the clear aqueous saline or dextrose solution, or by a mixture of the blood and the saline or dextrose solution. This is the physical basis of this invention. A preferred embodiment of a device used with the method employs an optical fiber illustrated in the FIGURE as follows:

Referring to the FIGURE, a light-emitting diode (LED) 2 generates interrogating light of wavelengths $\lambda_s$ within an absorption band of the hemoglobin of the red blood cells.

This light is injected into an optical fiber segment 4 and, through the fiber optic coupler 6, into the probe fiber 8. This fiber has a first (proximal) end connected to coupler 6 and a second (distal) end and includes a core 10 and a cladding 12. The cladding does not cover the core over a fiber segment S preferably less than 2 centimeters long at or near the fiber distal end, to which a light-reflecting layer 14 is applied. When the probe fiber is inside a blood vessel 16, preferably the pulmonary artery or the aorta, and the blood is flowing in the direction of the arrow 18, at least half of the intensity of the interrogating light is absorbed by the flowing red blood cells in optical contact with the unclad fiber segment, but a measurable amount of light is returned by the mirror 14 to the fiber coupler 6, the fiber segment 20 and the photodetector 22. Now a small volume of clear aqueous saline or dextrose solution is injected from a capillary tube 24 into the blood vessel at a distance D typically about ten centimeters or shorter from the fiber distal end in such a way that the blood flow carries the saline or dextrose solution, mixed with blood, towards the bare fiber core. The clear aqueous solution flows in the direction of arrow 18 and, after an interval $\Delta t$ usually shorter than fifty (50) seconds (typically near ten seconds), covers the unclad fiber segment after displacing from it most of the red blood cells previously covering it. Under these conditions the intensity of the interrogating light reaching the mirror 14 and being reflected towards the photodetector 22 is greatly increased.

The selected wavelength or wavelengths $\lambda_s$ are preferably those at which the absorption coefficient of the hemoglobin of the red cells is independent of the degree of oxygen saturation of the cells. This is the case for the wavelengths of 505 nm or 800 nm.

Instead of the light-reflecting layer 14 one may apply to the fiber distal end a photoluminescent layer. There a fraction of the intensity of the interrogating light transmitted by the bare fiber core is absorbed, generating luminescence light of wavelengths $\lambda_r$ different from $\lambda_s$.

Since changes may be made in the foregoing disclosure without departing from the scope of the invention herein involved, it is intended that all matter contained in the above description and depicted in the accompanying drawings be construed in an illustrative and not in a limiting case.

I claim:

1. A fiber optic method for measuring cardiac output, comprising the steps of:

(a) inserting into a blood vessel, when said vessel carries blood including hemoglobin-containing red cells flowing along it, an optical fiber having a proximal end and a distal end, the fiber having a core and a cladding around and in contact with said core over most of the length of the fiber, the fiber including a segment at or near the fiber distal end wherein the cladding does not cover the core, the core being bare but otherwise intact along the length of said segment;

(b) launching interrogating light of wavelengths $\lambda_s$, within an absorption band of the hemoglobin of said red blood cells and of pre-selected intensity into the fiber at the proximal end thereof, said light propagating along the fiber towards said distal end, at least a fraction of said intensity of said interrogating light being absorbed by said red blood cells;

(c) injecting into said blood vessel a clear aqueous solution at a distance from said bare segment of the fiber core such that said clear solution flows toward said bare segment under the action of the blood flow, thus causing an increase of the intensity of the interrogating light transmitted by said bare segment of the fiber core; and (d) sensing, with photodetector means, the increase of the intensity of the interrogating light transmitted by said bare segment of the fiber core.

2. A method as claimed in claim 1 wherein at least a fraction of the intensity of the interrogating light transmitted by said bare segment of the fiber core is reflected by a light-reflecting material at the distal end of said fiber and said reflected light is directed to said photodetector means.

3. A method as claimed in claim 1 wherein at least a fraction of the intensity of the interrogating light transmitted by said bare segment of the fiber core is converted to luminescence light of wavelengths $\lambda_r$ different from $\lambda_s$, by a photoluminescent material at the distal end of said fiber and part of the intensity of said luminescence light is directed to said photodetector means.

4. An arrangement for measuring cardiac output, comprising:

(a) an optical fiber having a proximal end and a distal end, the fiber having a core and a cladding around and in contact with said core over most of the fiber length, the fiber including a segment at or near the fiber distal end wherein the cladding does not cover the core, the core being bare but otherwise intact along the length of said segment;

(b) means for inserting said fiber into a bloodvessel carrying blood including hemoglobin-containing red cells flowing along it, (c) a light source for launching interrogating light of wavelengths $\lambda_s$ within an absorption band of the hemoglobin of said red blood cells and of pre-selected intensity into the fiber at the proximal end thereof, said light propagating along the fiber towards said distal end;

(d) means for injecting into said blood vessel a clear aqueous solution at a distance upstream from said bare fiber core such that said clear solution flows toward said bare core and reaches said bare fiber core in a time shorter than fifty seconds, thus causing an increase of the intensity of the interrogating light transmitted by said bare segment of the fiber core; and (e) photodetector means for sensing the changes in the intensity of the interrogating light transmitted by said bare fiber core as at least part of said clear solution flows over it.

5. An arrangement as claimed in claim 4 wherein the distal end of said fiber is terminated in a light-reflecting material and a fraction of said intensity of the interrogating light transmitted by said bare fiber core is reflected by said material toward said photodetector means.

6. An arrangement as claimed in claim 4 wherein the distal end of said fiber is terminated in a photoluminescent material and a fraction of said intensity of the interrogating light transmitted by said bare fiber core is absorbed by said photoluminescent material, thus generating luminescence light of wavelengths $\lambda_r$ different from $\lambda_s$, at least part of the intensity of which is directed by said fiber to said photodetector means.

\* \* \* \* \*